United States Patent [19]
Ferdman et al.

[11] Patent Number: 5,149,331
[45] Date of Patent: Sep. 22, 1992

[54] METHOD AND DEVICE FOR WOUND CLOSURE

[75] Inventors: Ariel Ferdman, 12 Hillside Ave., Melrose, Mass. 02176; Jing-wen Kuo, Boxboro, Mass.; David Miller, Brookline, Mass.; Vladimir Pinsky, Brighton, Mass.; William D. Richards, Medway, Mass.; David Swann, Cambridge, Mass.

[73] Assignee: Ariel Ferdman, Woburn, Mass.

[21] Appl. No.: 695,704

[22] Filed: May 3, 1991

[51] Int. Cl.[5] .................................. A61H 35/00
[52] U.S. Cl. ................................ 604/290; 604/291; 604/307; 604/902; 128/399; 601/27
[58] Field of Search ............. 604/289, 296, 291, 304, 604/308, 309-313, 89.1, 318, 316, 902; 128/155, 399, 400, 881, 390, 82, 82.1; 606/213, 215, 216, 27, 138, 148, 149

[56] References Cited

U.S. PATENT DOCUMENTS

| | | | |
|---|---|---|---|
| 3,026,874 | 3/1962 | Stevens | 604/305 |
| 3,486,504 | 12/1969 | Austin, Jr. | 604/313 |
| 4,540,412 | 9/1985 | Van Overloop | 604/307 |
| 4,759,354 | 7/1988 | Quarfoot . | |
| 4,969,880 | 11/1990 | Zamierowski | 604/308 |

Primary Examiner—Randall L. Green
Assistant Examiner—K. Reichle
Attorney, Agent, or Firm—Hale and Dorr

[57] ABSTRACT

A method of treating a wound site wherein a porous, adhesive backed dressing is utilized. A vacuum and/or heat is applied to the wound site through the dressing so as to draw the tissue adjacent the wound site to the dressing so as to minimize trauma to the wound and increase the adherence of the adhesive.

12 Claims, 1 Drawing Sheet

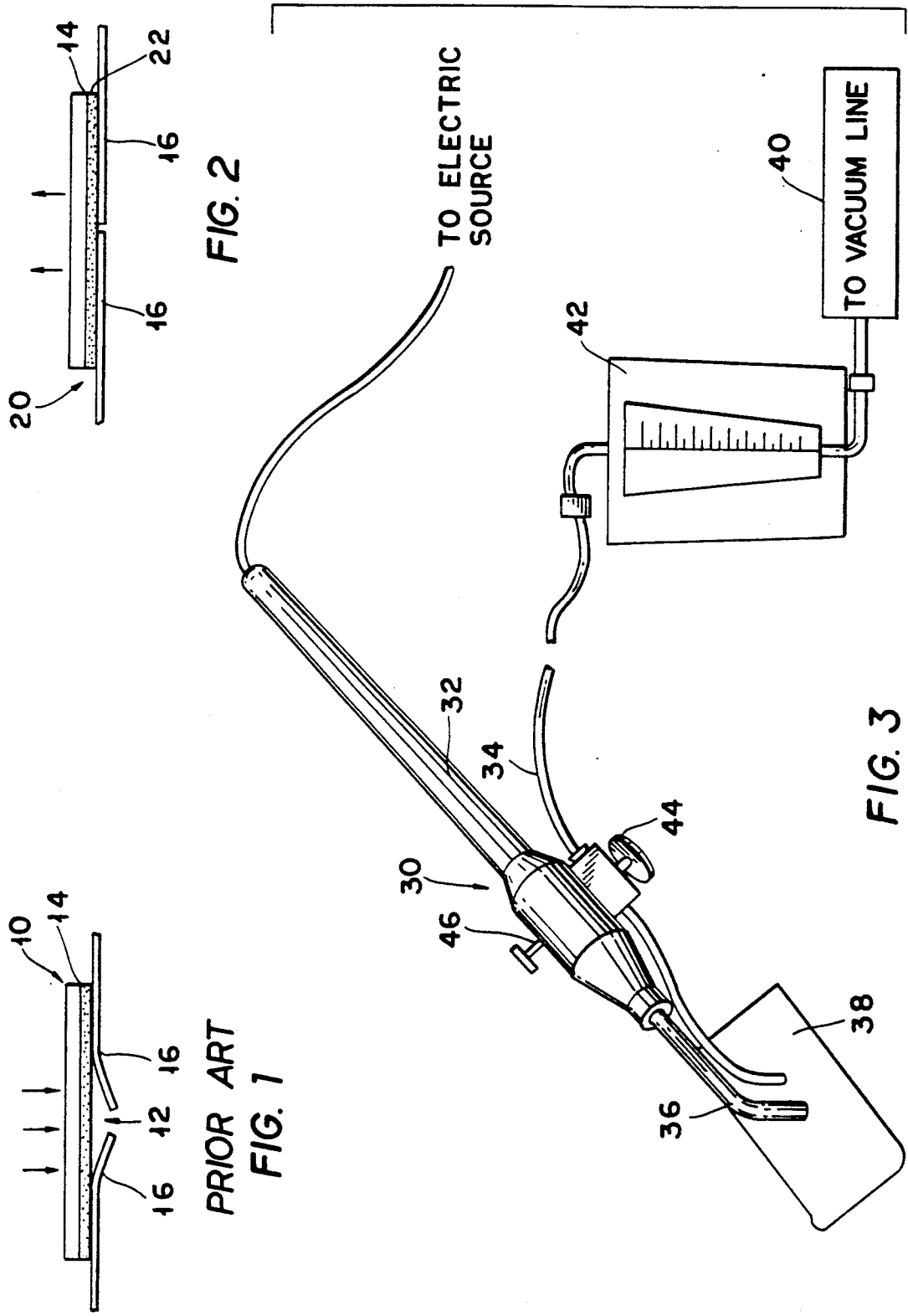

METHOD AND DEVICE FOR WOUND CLOSURE

BACKGROUND OF THE INVENTION

The present invention related to wound closures and in particular to an improved adhesive wound closure and method for applying the same.

In order to promote the healing of flesh wounds in humans and animals it is desireable to bring the severed surfaces of the wound into close contact with each other. Heretofore adhesive backed tapes such as the so-called "butterfly" bandages have been available as wound closures. Such devices, however, have two major problems associated with their use. The first problem arises from the difficulty in securing the adhesive to the tissue adjacent a wound without aggravating the wound since such dressings require that a pressure be applied to the dressing and hence to the wound. However, this is somewhat self defeating since applying a pressure to the tissue adjacent the wound tends to further separate the severed surfaces rather than draw them together. The second problem arises from the difficulty in obtaining a good adhesive bond between the dressing and the areas surrounding a wound as a result of the moist environment caused by the fluids excreted at the wound site.

Due to the existence of the above problems suturing has remained the preferred procedure for deep wound treatment notwithstanding the relative ease of using adhesive backed dressings in comparison to suturing.

SUMMARY OF THE INVENTION

In view of the above, it is the principle object of the present invention to provide an improved method for the treatment of wounds which enables the use of adhesive backed dressings while overcoming the problems associated with the use of such dressings as discussed above.

A further object is to provide a method of improving the flow characteristics of the adhesive of a dressing so as to minimize the contact force needed to obtain a good bond between the dressing and tissue.

A still further object is to provide a device which may be used in connection with the use of adhesive backed dressings in the treatment of wounds in accordance with the method of the present invention.

In accordance with the present invention a porous wound dressing provided with an adhesive backing is utilized. The contact side of the dressing is applied to the wound site and is heated as a vacuum is applied to the opposite side thereby improving the flow characteristics of the adhesive while drawing the tissue adjacent the wound site into contact with the adhesive. By drawing the tissue into contact with the dressing rather than pressing the dressing onto the wound the tissue adjacent the wound site is brought more closely to its natural state rather than being further separated as would be the case if the dressing were pressed against the wound site. Applying heat to the dressing also tends to drive moisture from the wound site to thereby improve the adherence of the dressing to the tissue at the wound site.

BRIEF DESCRIPTION OF THE DRAWINGS

In the accompanying drawings:

FIG. 1 is a simplified diagrammatic view of the effect on tissue adjacent a wound site of applying an adhesive backed dressing in accordance with prior art methodology.

FIG. 2 is a view similar to FIG. 1 illustrating the effect of the method of the present invention on the tissue adjacent a wound site.

FIG. 3 is a simplified view of a device which may be utilized in practicing the method of the present invention.

DETAILED DESCRIPTION OF THE PREFERRED EMBODIMENT

In the typical application of a dressing 10 to a wound 12 a downward force is applied to the dressing so as to cause a bonding between the adhesive 14 on the back of the dressing and the tissue 16 adjacent the wound. As shown in FIG. 1 a result of the downward force applied at the wound site is that the tissue adjacent the wound site flexes downwardly and actually widens the wound gap by separating the tissue further.

In accordance with a first aspect of the present invention a porous adhesive dressing 20 is utilized. The dressing 20 is lightly applied over the wound site and a vacuum is applied to the tissue adjacent the wound gap through the dressing thereby sucking the nonporous tissue adjacent the wound site into close contact and in bonding contact with the adhesive 22 as shown in FIG. 2. As a result of the wound tissue being brought into close contact the healing process is enhanced. To enable the vacuum to be applied through the dressing, the dressing must be porous. Such a porous dressing is disclosed, for example, in U.S. Pat. No. 4,759,354. One such porous dressing is available commercially from the 3M Corporation under the tradename "TRANSPORE."

As the tissue is sucked up against the dressing the dressing is preferably heated to between 40° C. and 80° C. This has two effects: firstly the application of heat to the dressing decreases the viscosity of the adhesive backing and thereby causes the adhesive to flow more uniformly and possibly into regions where it would not otherwise flow to improve the bonding with the tissue adjacent the wound. In addition, heating the dressing tends to dry the wound site and thereby improves the bonding between dressing and the tissue. A further benefit of applying heat is derived from the generally soothing effect that the additional warmth has on a possibly traumatized patient.

In a successful test of the invention a 2.6 mm×4.0 mm strip of TRANSPORE tape was applied to a section of skin and subjected to a vacuum which when open had a negative air flow of 1 SCFM (standard cubic foot per minute) and heated through a range of temperatures. Optimum results were obtained when the dressing was heated to a temperature of 55° C. When the heat and vacuum were both applied to the dressing the force of adherence was increased by a factor of approximately 2.4 as compared with no heat or vacuum being applied. When only a vacuum was applied to the dressing the adherence was increased by a factor of approximately 1.6. When only heat was applied the adherence appeared to increase with temperature but leveled off at 80° C. with an increased adherence factor of 2.3. At 55° C. the adherence increased by a factor of 1.8.

Reference is now made to FIG. 3 wherein a device is depicted with which the present invention may be practiced. The device 30 includes a grip 32 supporting both a suction line 34 and a heating rod 36. The heating rod terminates in a plate 38 through which the suction line 34 passes. The suction line is connected to a vacuum pump 40 through a flow meter 42 and control valve 44. Similarly a control element 46, in the form of a rheostat or the like, is provided to control the temperature attained by the heating element 36.

In use the porous dressing is applied over the wound and thereafter the device 30 is slightly passed over the dressing without bearing down on the dressing. The effect of the vacuum is to draw the tissue to the adhesive backing of the dressing rather than the reverse. The applied heat in addition to assisting in the drying of fluids at the wound site and improving the adhesive characteristics of the adhesive backing has been reported as having a soothing effect thereby possibly minimizing trauma to the patient.

Thus, in accordance with the above, the aforementioned objectives may effectively be attained.

Having thus described the invention what is claimed is:

1. A method of treating a would comprising the steps of:
    applying a porous, adhesive backed dressing to a wound site; and
    applying a vacuum to said wound site through said porous dressing to draw the tissue adjacent the wound into bonding contact with said adhesive without depressing said dressing into the wound.

2. The method in accordance with claim 1 wherein, the step of vacuum application further includes generating said vacuum with a vacuum line which when open has a negative air flow of approximately 1 standard cubic foot per minute or greater.

3. The method in accordance with claim 1 comprising the further step of applying heat to said dressing to cause said adhesive to flow and to drive moisture from the wound site and thereby improve bonding contact between said dressing and the tissue without depressing said dressing into the wound.

4. The method in accordance with claim 3 wherein said step of vacuum application is performed simultaneously with said step of heat application.

5. The method in accordance with claim 3 wherein said step of heat application further includes heating said dressing to between 40° C. and 80° C.

6. The method in accordance with claim 4 wherein said step of vacuum application is performed simultaneously with said step of heat application.

7. A method of treating a wound comprising the steps of:
    applying a porous, adhesive backed dressing to a wound site; and
    applying heat to said dressing through said porous dressing to cause said adhesive to flow and to drive moisture from the wound site and thereby improve bonding contact between said dressing and the tissue adjacent the wound site without depressing said dressing into the wound.

8. The method in accordance with claim 7 wherein said step of heat application further includes heating said dressing to be between 40° C. and 80° C.

9. A device for use with a porous, adhesive backed dressing for treating a wound site, said device including:
    vacuum means for applying suction to said wound site through said porous dressing to draw the tissue adjacent the wound site into bonding contact with said adhesive without depressing said dressing into the wound; and grip means for supporting said vacuum means.

10. A device in accordance with claim 9 further comprising a plate affixed to said grip means, and said vacuum means passing through said plate.

11. The device in accordance with claim 10 further comprising means for heating said plate so that heat is applied to the dressing to cause said adhesive to flow and to drive moisture from the wound site and thereby improve bonding contact between said dressing and the tissue without depressing said dressing into the wound.

12. A device for use with an adhesive backed porous dressing for treating a wound site said device including:
    a grip;
    a plate affixed to said grip; and means for heating said plate so that heat is applied through said porous dressing to cause said adhesive to flow and to drive moisture from the wound site and thereby improve bonding contact between said dressing and the tissue adjacent the wound site without depressing said dressing into the wound.

* * * * *